United States Patent
Wang

(10) Patent No.: US 9,020,252 B2
(45) Date of Patent: Apr. 28, 2015

(54) IMAGE RECOGNITION METHOD AND IMAGE RECOGNITION SYSTEM

(71) Applicant: National Taiwan University of Science and Technology, Taipei (TW)

(72) Inventor: Ching-Wei Wang, Taipei (TW)

(73) Assignee: National Taiwan University of Science and Technology, Taipei (TW)

(*) Notice: Subject to any disclaimer, the term of this patent is extended or adjusted under 35 U.S.C. 154(b) by 90 days.

(21) Appl. No.: 13/829,331

(22) Filed: Mar. 14, 2013

(65) Prior Publication Data

US 2014/0112578 A1 Apr. 24, 2014

(30) Foreign Application Priority Data

Oct. 19, 2012 (TW) ................ 101138719 A

(51) Int. Cl.
*G06K 9/00* (2006.01)
*G06K 9/46* (2006.01)
*A61B 8/08* (2006.01)
*G06T 7/00* (2006.01)

(52) U.S. Cl.
CPC ............ *G06K 9/4652* (2013.01); *A61B 8/0866* (2013.01); *G06T 7/0083* (2013.01); *G06T 2207/10132* (2013.01); *G06T 2207/30044* (2013.01)

(58) Field of Classification Search
CPC ............. G06T 7/408; G06T 2207/10024; G06T 7/0081; G06T 11/001; G06T 5/001; G06K 9/4652; G06F 17/30243; H04N 1/6058
USPC .......... 382/101, 113, 153, 165, 162, 181.199; 331/158, 108 C, 116 M; 340/5.53; 347/19, 37; 356/328; 358/538, 530; 701/28, 409, 533; 707/737, 802
See application file for complete search history.

(56) References Cited

U.S. PATENT DOCUMENTS

| | | | | |
|---|---|---|---|---|
| 5,287,204 A | * | 2/1994 | Koizumi et al. | 358/538 |
| 6,816,611 B1 | * | 11/2004 | Hagiwara et al. | 382/165 |
| 6,832,824 B1 | * | 12/2004 | Baker et al. | 347/19 |
| 8,922,651 B2 | | 12/2014 | Huang et al. | |

FOREIGN PATENT DOCUMENTS

| CN | 102135417 A | 7/2011 |
|---|---|---|
| CN | 102542572 A | 7/2012 |

OTHER PUBLICATIONS

"Extracting the contour of B-ultrasonic cross sectional images" Journal of Tianjin University vol. 33, No. 3. May 31, 2000.

* cited by examiner

*Primary Examiner* — Anh Do
(74) *Attorney, Agent, or Firm* — Birch, Stewart, Kolasch & Birch, LLP

(57) ABSTRACT

An image recognition method and an image recognition system can be applied to fetal ultrasound images. The image recognition method includes: (a) adjusting the image with a filter operator to decrease noise and to homogenize an image expression level of the pixel units within an individual object structure; (b) analyzing the image by a statistic information function, determining a foreground object pixel unit and a background pixel unit according to a max information entropy state of the statistic information function; and (c) searching by a profile setting value and recognizing a target object image among the foreground object pixel unit. The image recognition method can not only increase the efficiency of identifying the object of interests within the image and measuring the object of interests, but also improve the precision of measurements of the object of interests.

20 Claims, 15 Drawing Sheets

IMAGE RECOGNITION METHOD AND IMAGE RECOGNITION SYSTEM

BACKGROUND OF THE INVENTION

1. Field of the Invention

The present invention relates generally to an image recognition method and an image recognition system; especially, the present invention relates to a method and a system which can automatically recognize, analyze, and measure ultrasound images, wherein the ultrasound images include fetal ultrasound images; particularly, the present invention relates to an image recognition, analysis, measuring method and a system which can analyze the image, increase recognition efficiency, and automatically conduct the measurement.

2. Description of the Prior Art

Ultrasound detection has advantages of real-time, low cost, easy use, and non-invasion and is widely applied in biomedicine field, particularly to detect the fetal growth in the uterus. Generally, doctors utilize an ultrasound detector detecting ultrasound dynamic images of fetus and try to retrieve the real-time image from best angle. In practical applications, the ultrasound detector has an image recognition system, wherein the image recognition system can read contents of the retrieved real-time image and provide a plurality of image analysis tools. However, the image analysis tools need to be operated manually by users to interpret the contents of the images and to manually measure the contents of the images.

For instance, doctors need to search target images with naked eyes, wherein the target images include a skull image, a femur image, or other organ images. It is noted that the search result of the visual method is easy to generate inaccuracy and inconsistency when the target image is too fuzzy, so that the doctor is hard to determine the correct position of the target image, further influencing the determined result of the target image.

In addition, the doctor drags a scale tool to manually measure a length of the target image when the target image is processed by the image analysis tool. It is noted that measurement conducted by manually dragging the scale tool is subjective, inconsistent, time-consuming and cannot effectively provide a better medical quality. In addition, if the determined result of the target image generates large error, the subsequent dimension measurement will be influenced. For the above reasons, the conventional image cognition system still has many defects.

SUMMARY OF THE INVENTION

In view of prior art, the present invention provides an image recognition method and an image recognition system, which can analyze images, increase recognition efficiency, and conduct image measurement, especially to analyze ultrasound images.

It is an object of the present invention to provide an image recognition method having a statistic information function to increase image recognition efficiency.

It is an object of the present invention to provide an image recognition method utilizing matrices to analyze an edge of an object to detect a target object image.

It is an object of the present invention to provide an image measuring method to transform a measured result into the dimension (transforming a pixel unit into a physical dimension unit (mm)) to increase image measuring efficiency.

It is an object of the present invention to provide an image recognition system, which can automatically segment biological structures of fetal ultrasound images and generate the biometric fetal measurements rapidly to increase image analysis accuracy.

It is an object of the present invention to provide an image recognition medium, wherein the image recognition medium stores an image recognition method or an image recognition system to recognize objects of interests in images and measure the objects of interests within images.

The present invention provides an image recognition method for recognizing objects of interests in an image including a plurality of pixel units, the image recognition method includes: (a) adjusting the image with a filter operator to decrease noise and to homogenize an image expression level of the pixel units within an individual object structure; (b) analyzing the image by a statistic information function, determining a foreground object pixel unit and a background pixel unit according to a max information entropy state of the statistic information function; and (c) searching by a profile setting value and recognizing a target object image among the foreground object pixel unit. In practical applications, the target object image can be a tissue image, a structure image, or an organ object image, but is not limited to the embodiment.

The present invention provides an image recognition method for recognizing an image, including: (a) detecting a directional edge of the image by an edge operator; (b) enhancing the directional edge; (c) inverting a color level; and (d) searching a target object image by a profile setting value, wherein the profile setting value corresponds to a connected object. In an embodiment, the directional edge is a horizontal direction edge, but is not limited thereto.

The present invention provides an image recognition system for recognizing objects of interests in an image including a plurality of pixel units, the image recognition system includes an image operating module, an analysis module, and a recognizing module. The image operating module has a filter operator, wherein the filter operator adjusts the image to decrease noise and homogenizes an image expression level of the pixel units within an individual object structure. The analysis module is connected with the image operating module and stores a first operating mode, wherein the first operating mode has a statistic information function, and the analysis module analyses the image by the statistic information function and classifies the pixel units into a foreground object pixel unit and a background pixel unit in the first operating mode. In addition, the image recognizing module chooses an optimum object as a target object based on the morphology and layout of the object.

Compared to prior arts, the image recognition method and the image recognition system of the present invention utilize the statistic information function to define the pixel unit to recognize the target object image, further increasing image recognition efficiency. In addition, the image recognition method analyzes the image by the edge operator and recognizes the target object image by the profile setting value. In practical applications, the image recognition system has the function of measuring the image, the completion time of the process of analyzing, recognizing, and measuring is averagely 2.28 seconds.

The detailed descriptions and the drawings thereof below provide further understanding about the advantage and the spirit of the present invention.

DETAILED DESCRIPTION OF THE PREFERRED EMBODIMENT

An embodiment of the present invention provides an image recognition method, which is applied to recognize an image. In the embodiment, the image can be an ultrasound image, such as fetal ultrasound image, but not limited thereto.

Figure 1:
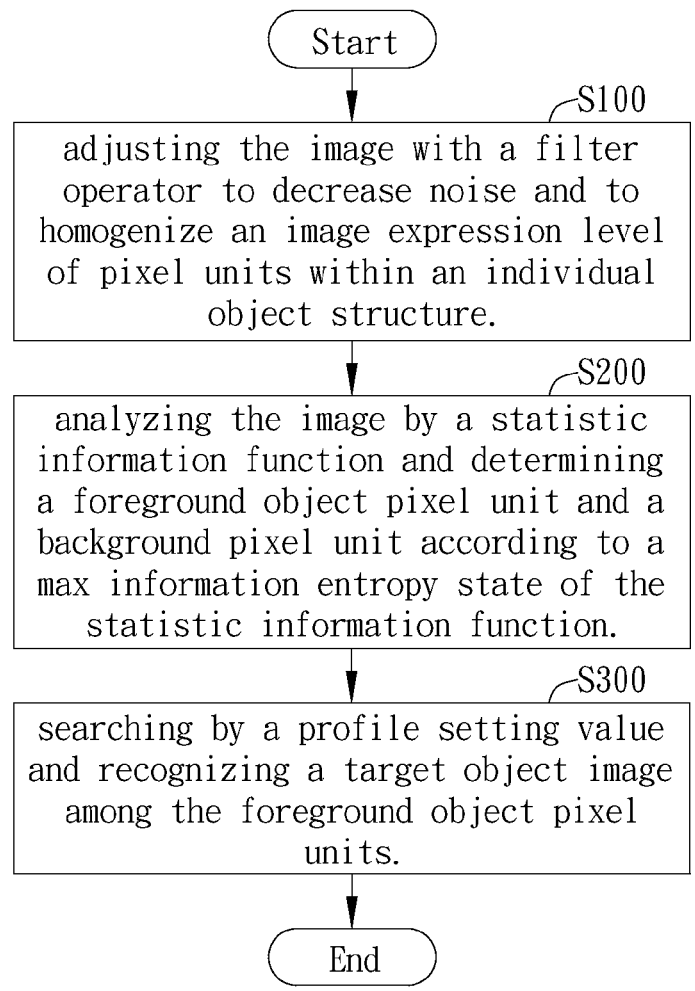
FIG. 1 is a flowchart of an embodiment of an image recognition method of the present invention.

Please refer to FIG. 1; FIG. 1 is a flowchart of an embodiment of an image recognition method of the present invention. As shown in FIG. 1, the image recognition method firstly executes a step S100, adjusting the image with a filter operator to decrease noise and to homogenize an image expression level of pixel units within an individual object structure. In practical applications, the image includes a plurality of pixel units, wherein the pixel units are pixel elements disposed with matrix arrangement. In an original image, color variation of the pixel units is extremely large, and the filter operator can decrease the variation of image and sharpen or smooth the image to simplify the structure information of the image. In practical applications, the filter operator can be an image operating matrix and can adjust color block of each pixel unit, but not limited to the embodiment. In other words, the filter operator can decrease undesired noises of the image and is a pre-process of the image recognition.

Then, the image recognition method executes the step S200, analyzing the image by a statistic information function and determining a foreground object pixel unit and a background pixel unit according to a max information entropy state of the statistic information function. It is noted that the statistic information function is an image analysis tool, which can filter the image greatly to achieve the effect of recognizing the image. Implements of the statistic information function and the max information entropy state will be illustrated in greater detail in other embodiments of the present invention.

Then, the image recognition method executes the step S300, searching by a profile setting value and recognizing a target object image among the foreground object pixel units. It is noted that the target object image includes images of skull, femur, or other organs, wherein each organ corresponds to a profile setting value. For instance, the profile of femur is an elongated structure, and the skull has a circular-like structure, wherein the femur and the skull respectively correspond to a femur profile setting value and a skull profile setting value, so that the image recognition method recognizes the femur target image or the skull target image according to the femur profile setting value and the skull profile setting value. In addition, in the process, the image recognition method can define the profile setting value by two ends of the femur elongated structure having circular profile to recognize the target object image.

Figure 2A:
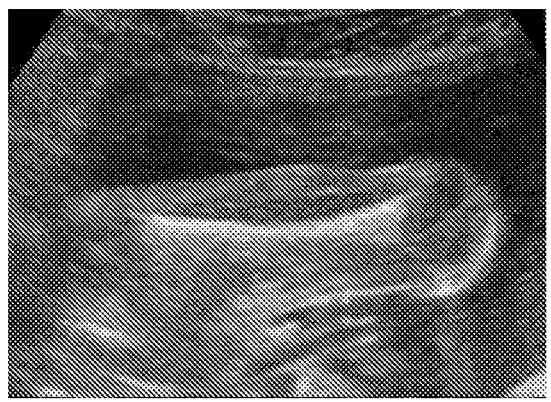
FIG. 2A is a schematic view of the original image of the present invention.
Figure 2B:
FIG. 2B is a schematic view of the operated image of the statistic information image of the present invention.
Figure 2C:
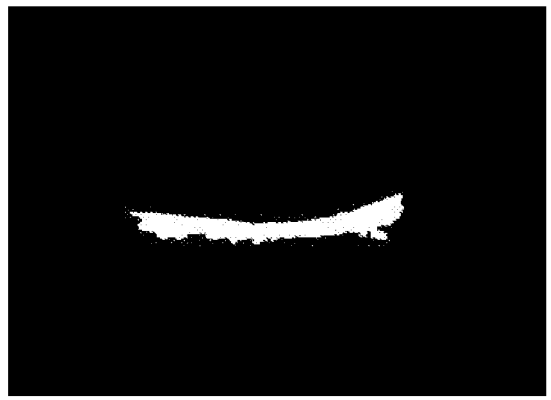
FIG. 2C is a schematic view of an image of the recognized target object of the present invention.

For instance of the femur target image, please refer to FIG. 2A through FIG. 2C, wherein FIG. 2A is a schematic view of the original image of the present invention; FIG. 2B is a schematic view of the operated image of the statistic information image of the present invention; FIG. 2C is a schematic view of an image of the recognized target object of the present invention. In practical applications, the user can retrieve the ultrasound image by an ultrasound detecting apparatus. FIG. 2A shows the original image of the ultrasound image. It is noted that after the image recognition method executes the steps S100 and S200, the image shown in FIG. 2B has a clear femur profile and other similar profiles. In addition, after the image recognition method executes the step S300, the image recognition method can recognize the femur target image as shown in FIG. 2C.

Figure 3:
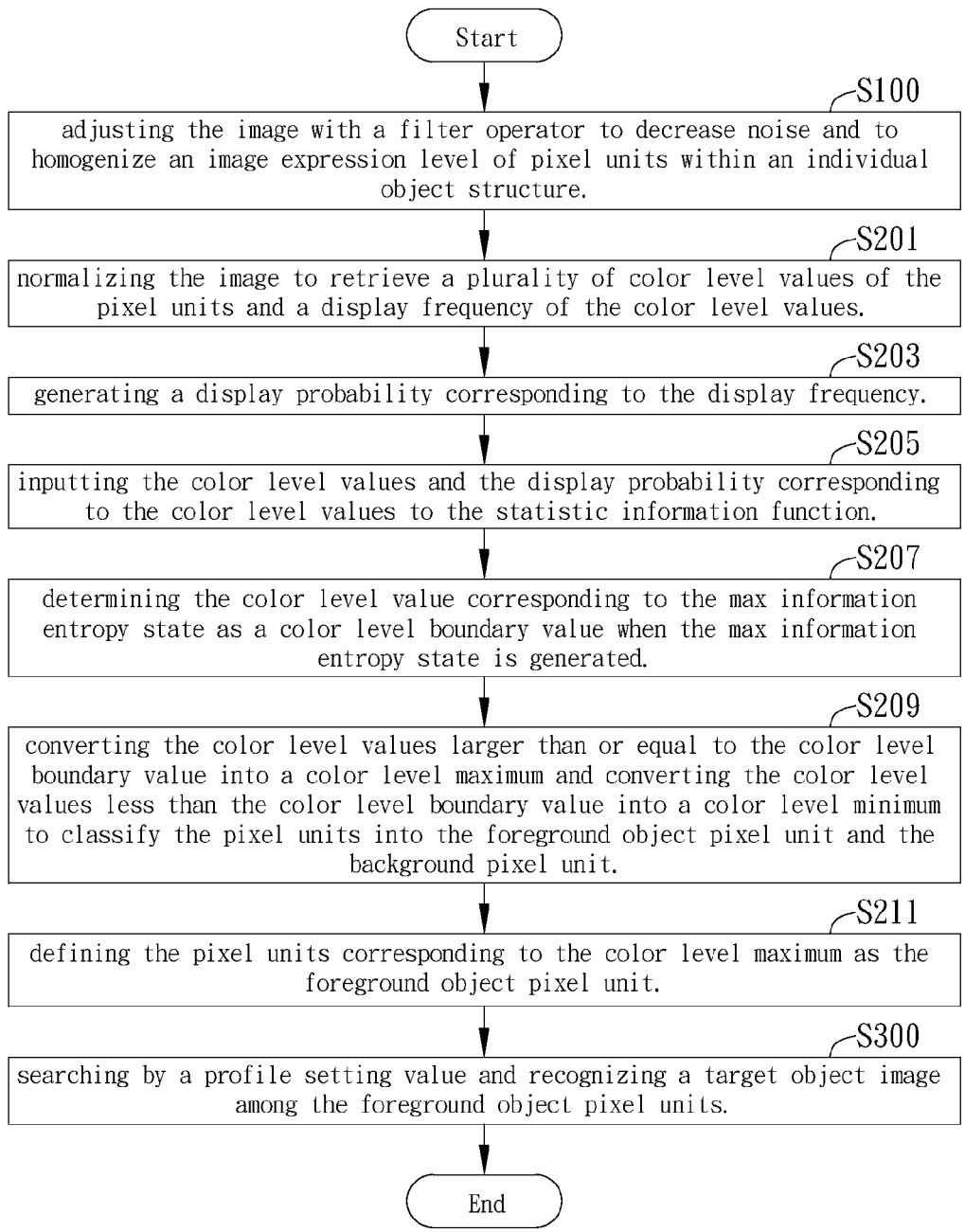
FIG. 3 is a flowchart of another embodiment of the image recognition method of the present invention.

In addition to the image recognition method of FIG. 1, the present invention illustrates the analysis process of the statistic information function by several steps. Please refer to FIG. 3; FIG. 3 is a flowchart of another embodiment of the image recognition method of the present invention. As shown in FIG. 3, after the step S100, the image recognition method executes the step S201, normalizing the image to retrieve a plurality of color level values of the pixel units and a display frequency of the color level values. Particularly, the range of the color level values is $0 \sim 2^c - 1$, wherein the color corresponding to the color level value of 0 is black, and the color corresponding to the color level value of $2^c - 1$ is white. c is a bit number and is for encoding the image expression level of the pixel units. For instance of an 8-bit ultrasound image, wherein c=8; for a 16-bit ultrasound image, wherein c=16. In the process, the image recognition method retrieves the color level value of each pixel unit, and the display frequency of each color level value is the frequency of occurrence of each color level value.

Then, the image recognition method executes the step S203, generating a display probability corresponding to the display frequency. It is noted that, in the step S201, the method acquires the display frequency of each color level value, and the step S203 generates the probability of occurrence of each color level value which is defined as the display probability.

Then, the image recognition method executes the step S205, inputting the color level values and the display probability corresponding to the color level values to the statistic information function. In the method, the statistic information function is an entropy information function, but not limited to the embodiment. Furthermore, the image recognition method utilizes the entropy information function to determine usable pixel units, further recognizing the target object image.

For instance, after the image recognition method executes normalizing the image, the display probability P and the range thereof $p_0 \sim p_{2^c-1}$ are acquired wherein the range of the color level value j is 0 to $2^c-1$, and the image entropy H(P) can be given from equations [1]~[4]:

$$H(A) = -\sum_{i=0}^{j} p_i \log p_i; \quad [1]$$

$$H(B) = -\sum_{i=j}^{2^c-1} p_i \log p_i; \quad [2]$$

$$H_j = -\log P(A) - \log P(B) - \frac{H(A)}{P(A)} - \frac{H(B)}{P(B)}; \text{ and} \quad [3]$$

$$j = \operatorname{argmax} H_j \big|_{j=0 \sim 2^c-1}; \quad [4]$$

wherein the color level value $j \in \{0 \ldots 2^c-1\}$, $A \in \{0 \ldots j\}$, $B \in \{2^c-1 \ldots j\}$.

Then, the image recognition method executes the step S207, determining the color level value corresponding to the max information entropy state as a color level boundary value when the max information entropy state is generated. In the method, the image recognition method determines the color level value corresponding to the max information entropy state as the color level boundary value when the statistic information function generates the max information entropy state. It is noted that the color level boundary value is a classified color level boundary value between the foreground object pixel unit and the back pixel unit. Furthermore, the image recognition method computes the color level boundary value, which can identify the foreground and background, through the equations [1]~[4], further determining the required foreground object pixel unit.

The image recognition method executes the step S209, converting the color level values larger than or equal to the color level boundary value into a color level maximum and converting the color level values less than the color level boundary value into a color level minimum to classify the pixel units into the foreground object pixel unit and the background pixel unit. It is noted that the color level maximum is $2^c-1$, which corresponds to white; the color level minimum is 0, which corresponds to black. For instance, as shown in FIGS. 2A and 2B, the color level value which is larger than or equal to the color level boundary value is converted into white, and the color level value which is less than the color level boundary value is converted into black. In addition, for the 8-bit image, c is 8, and the color level maximum is 255.

Then, the image recognition method executes the step S211, defining the pixel units corresponding to the color level maximum as the foreground object pixel unit. The method can execute advanced image recognition by defining the pixel units as the foreground object pixel unit. In addition, as described above, the method utilizes the step S300 to recognize the target object image among the chosen pixel units. It is noted that the image recognition method of the present invention utilizes the entropy information function to determine the color level boundary value to increase image recognition efficiency.

Figure 4:
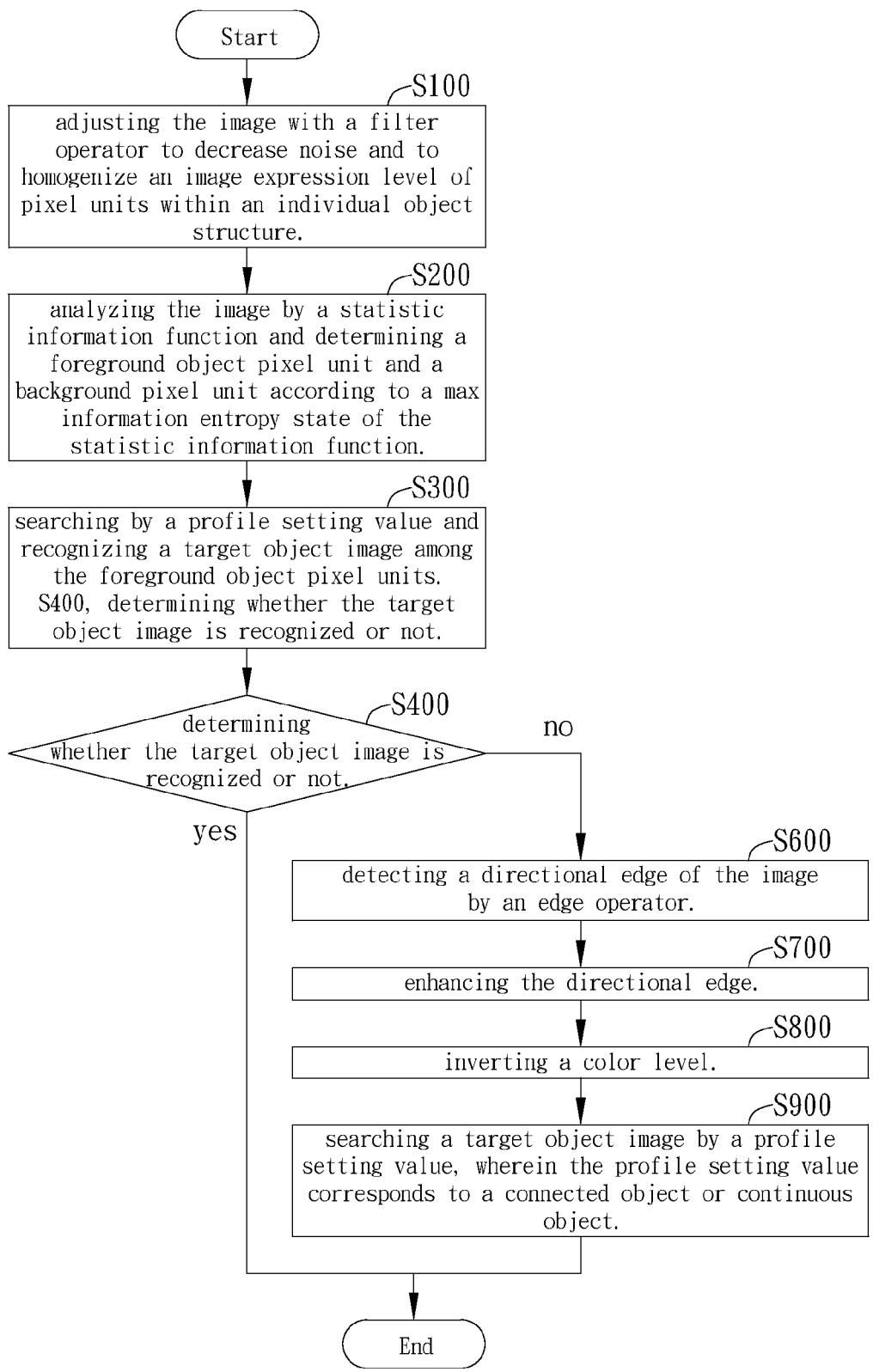
FIG. 4 is a flowchart of another embodiment of the image recognition method of the present invention.

Please refer to FIG. 4; FIG. 4 is a flowchart of another embodiment of the image recognition method of the present invention. As shown in FIG. 4, after the step S300, the image recognition method executes the step S400, determining whether the target object image is recognized or not. The method executes the step S600 if the target object image is not recognized in step S300. In practical applications, the image recognition method may filter out too much effective information in the step S100, so that the subsequent image recognition fails. As such, the method requires another recognition process. In other words, if the target object image cannot be recognized in the steps S100 through S400 of the image recognition method, the image recognition method executes the step S600, detecting a directional edge of the image by an edge operator. It is noted that the directional edge can be a horizontal direction edge, a vertical direction edge, or an oblique direction edge. In the embodiment, the directional edge can be a horizontal direction edge. It is noted that the step S600 does not utilize the filter operator of the step S100 to execute the pre-process of the image and can retain details of the original image. In other words, the steps S600 through S900 execute computations directly from the color level values of the pixel units of the original image and have high recognition efficiency.

In addition, the edge operator can be a matrix operator, especially is a convolution operator. For instance of the femur target image, the correlation between the edge operator and the original image is given as:

$$I = I_s^* \begin{bmatrix} 1 & 2 & 1 \\ 0 & 0 & 0 \\ -1 & -2 & -1 \end{bmatrix};$$

wherein I is a computed image, Is is the original image, and the matrix operator is the edge operator. In the process, because the femur object in the image has horizontal direction, the edge operator detects the edge in horizontal direction to detect the position of the femur.

Figure 5A:
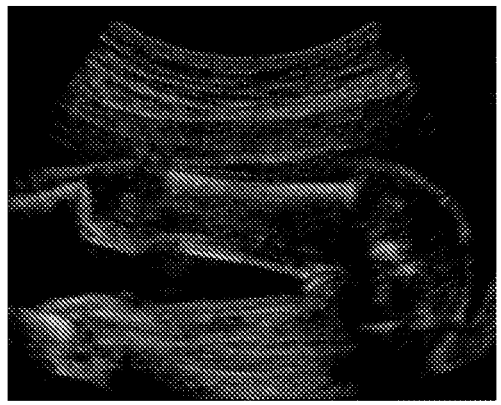
FIG. 5A is a schematic view of the original image of the present invention.
Figure 5B:
FIG. 5B is a schematic view of an image with enhanced directional edge of the present invention.

Then, the image recognition method executes the step S700, enhancing the directional edge. Please refer to FIGS. 5A and 5B; FIG. 5A is a schematic view of the original image of the present invention; FIG. 5B is a schematic view of an image with enhanced directional edge of the present invention. As shown in FIGS. 5A and 5B, after the enhancement, the profile of the directional edge is clearly sharper.

Figure 5C:
FIG. 5C is a schematic view of an image of the recognized target object of the present invention.

In addition, the image recognition method executes the step S800, inverting a color level, and the step S900, searching a target object image by a profile setting value, wherein the profile setting value corresponds to a connected object or continuous object. Please refer to FIG. 5C; FIG. 5C is a schematic view of an image of the recognized target object of the present invention. In the process, the target object image is the femur, but not limited to the embodiment. As shown in FIGS. 5B and 5C, the femur object of FIG. 5B is a black continuous elongated structure; after the color level is inverted, the femur object of FIG. 5C is a white continuous elongated structure. It is noted that the femur target object image of FIG. 5C is the result after searching by the profile setting value. Detailed descriptions of the profile setting value and the process thereof of the step S900 are essentially the same as the step S300 and not elaborated hereinafter.

Figure 6A:
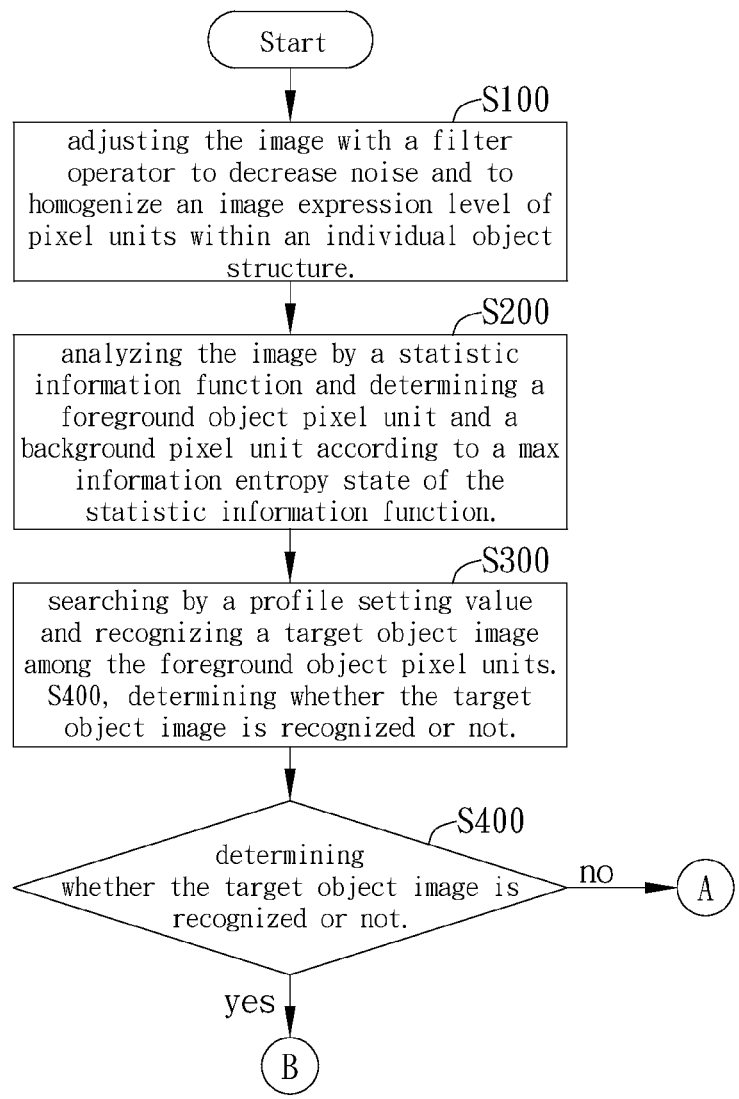
FIG. 6A is a flow chart of another embodiment of the image recognition method of the present invention.
Figure 6B:
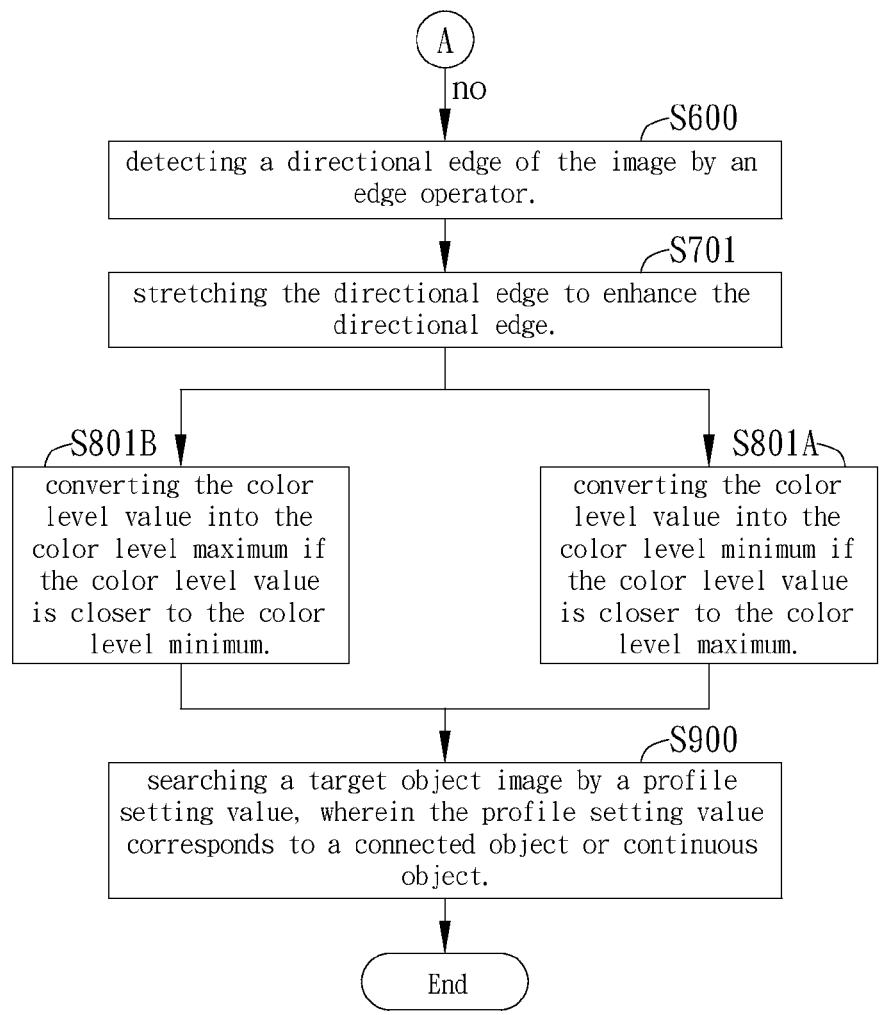
FIG. 6B is a flow chart of another embodiment of the image recognition method of the present invention.

In addition to the image recognition method of FIG. 4, the present invention illustrates the analysis process of the edge operator by several steps. Please refer to FIGS. 6A and 6B; FIG. 6A is another embodiment of the image recognition method of the present invention; FIG. 6B is another embodiment of the image recognition method of the present invention. As shown in FIGS. 6A and 6B, after the step S600, the image recognition method executes the step S701, stretching the directional edge to enhance the directional edge.

In the process of the step S600, stretching the directional edge can be given from equations [5]~[7]:

$$G_x = I^* \begin{bmatrix} 1 & 0 & -1 \\ 2 & 0 & -2 \\ 1 & 0 & -1 \end{bmatrix}; \quad [5]$$

$$G_y = I^* \begin{bmatrix} -1 & -2 & -1 \\ 0 & 0 & 0 \\ 1 & 2 & 1 \end{bmatrix}; \quad [6]$$

$$I^* = \sqrt{G_x^2 + G_y^2}; \quad [7]$$

wherein Gx is a transverse operator, Gy is a longitudinal operator, and the step S701 utilizes these two operators to enhance the directional edge of the image to increase the sharpness and the contrast of the structure of directional edge. It is noted that the color level of the femur object of the FIG. 5A is not the same as the color level of the FIG. 5B. As such, the method requires executing the step S801A and the step S801B. It is noted that the image includes the pixel units, wherein each pixel unit has the color level value, and the color level value is between a color level maximum and a color level minimum.

In the process, the image recognition method executes the step S801A, converting the color level value into the color level minimum if the color level value is closer to the color level maximum, and the step S801B, converting the color level value into the color level maximum if the color level value is closer to the color level minimum. As described above, the color level maximum is $2^c-1$, which corresponds to white; the color level minimum is 0, which corresponds to black. In other words, if the original color level value is closer to white, then it is converted into black; if the original color level value is closer to black, then it is converted into white. As shown in FIGS. 5B and 5C, after converting the color level and recognizing the target object image, the image recognition method can acquire a precise result. Compared to the image recognition method of FIGS. 1 and 3, the image recognition method of FIGS. 4, 6A, and 6B can increase the recognition efficiency of the target object image, further increasing the image recognition efficiency.

Figure 7:
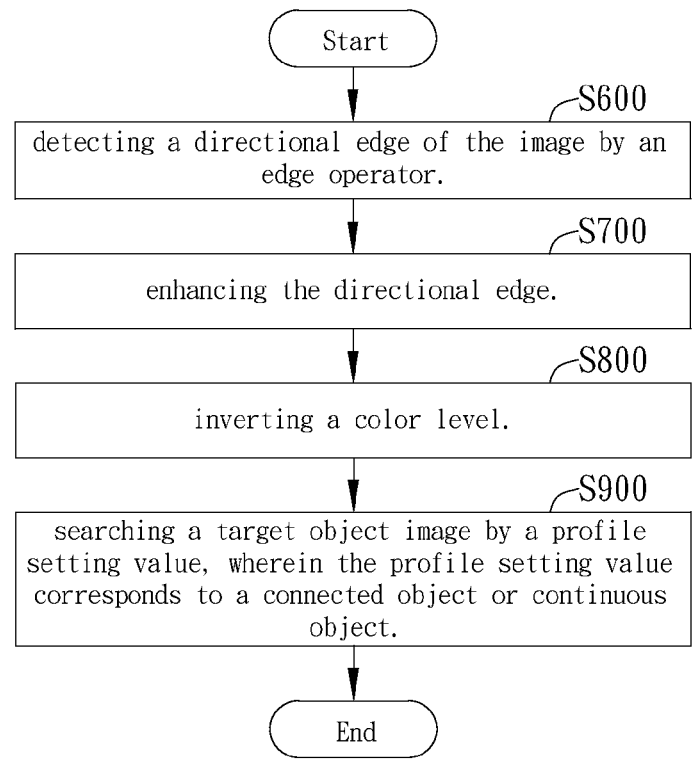
FIG. 7 is a flowchart of the embodiment of the image recognition method of the present invention.

It is noted that, in other processes, the image recognition method can skip the steps S100 through S400 and just executes the steps S600 through S900 of FIG. 4 or the steps S600 through S900 of FIGS. 6A and 6B. For instance, please refer to FIG. 7; FIG. 7 is a flowchart of the embodiment of the image recognition method of the present invention. As shown in FIG. 7, the image recognition method only involves the processes of steps S600 through S900 of FIG. 4. In other words, the image recognition method can just utilize the edge operating method to execute the image detection without utilizing the analysis method of the statistic information function, but not limited to the embodiment.

Figure 8A:
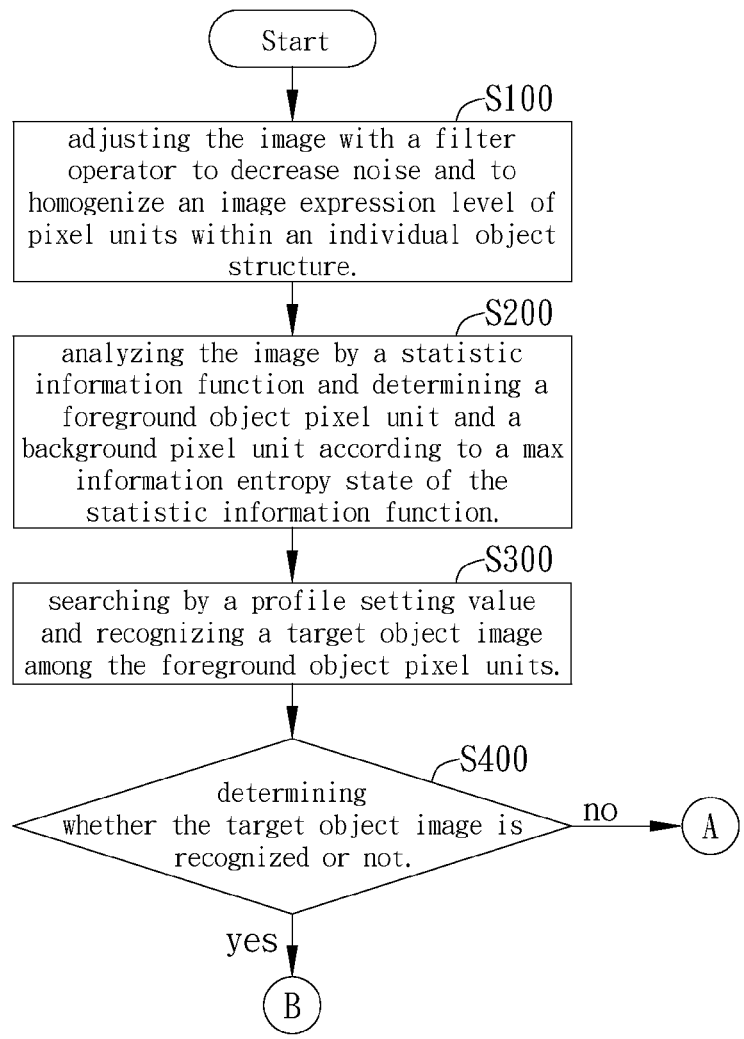
FIG. 8A is a flowchart of another embodiment of the image recognition method of the present invention.
Figure 8B:
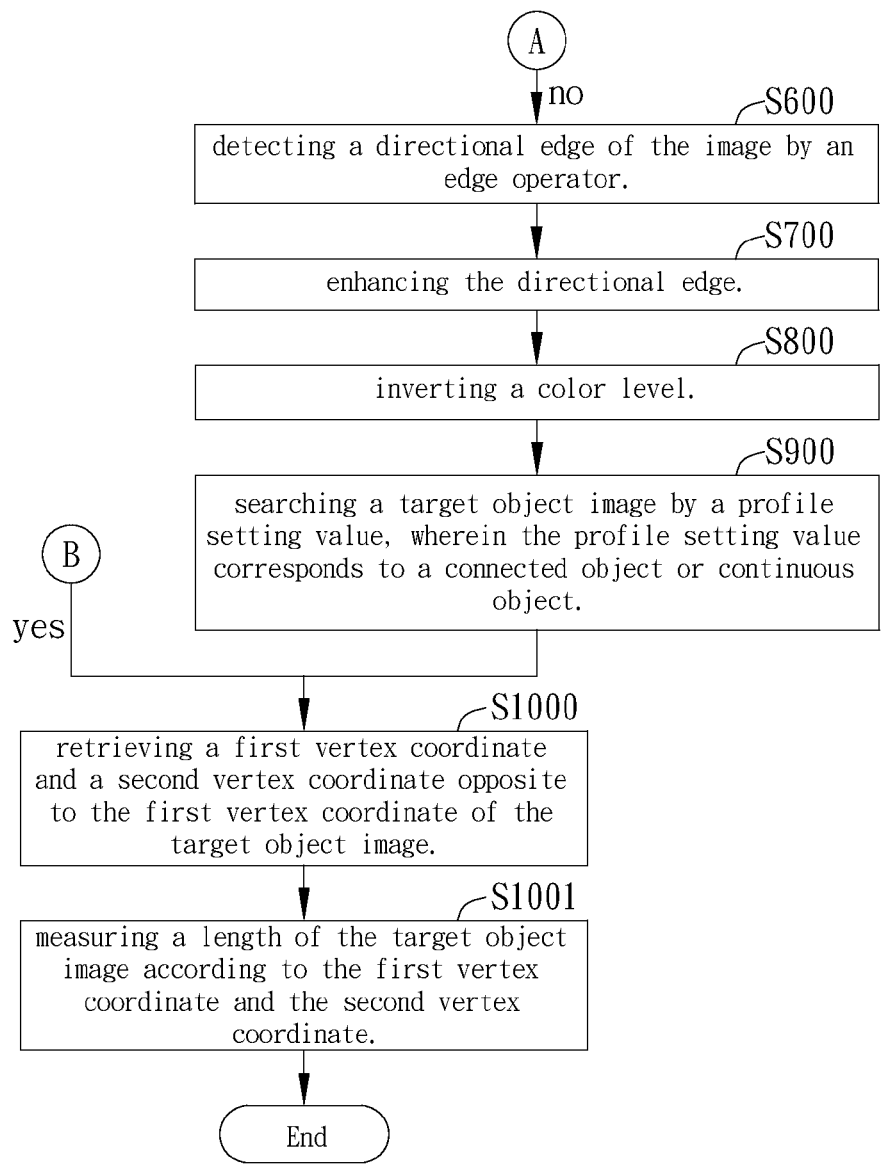
FIG. 8B is a flowchart of another embodiment of the image recognition method of the present invention.

In addition, the present invention further provides an advanced embodiment to illustrate the image recognition method which can increase the measuring efficiency. Please refer to FIGS. 8A and 8B; FIG. 8A is a flowchart of another embodiment of the image recognition method of the present invention; FIG. 8B is a flowchart of another embodiment of the image recognition method of the present invention. As shown in FIGS. 8A and 8B, compared to the process of FIG. 4, after the step S400 or the step S900, the method of FIGS. 8A and 8B executes the step S1000, retrieving a first vertex coordinate and a second vertex coordinate opposite to the first vertex coordinate of the target object image. For instance of the femur target object image, the first vertex coordinate and the second vertex coordinate are the coordinates of two ends of the femur object.

Then, the image recognition method executes the step S1001, measuring a length of the target object image according to the first vertex coordinate and the second vertex coordinate. For instance, the distance between the first vertex coordinate and the second vertex coordinate can be computed by the distance calculation means, and the image recognition method can acquire the length of the target object image. Particularly, the image recognition method of FIGS. 8A and 8B can measure the dimension of the target object image. In addition, the step S1000 and the step S1001 can be executed in combination with the image recognition methods of FIGS. 1, 3, 6A, 6B, and 7 according to practical requirements to achieve the effect of dimension measurement. Particularly, the step S1000 and the step S1001 can be executed after the step S300 of FIG. 1, the step S300 of FIG. 3, the step S400 or the step S900 of FIGS. 6A and 6B, or the step S900 of FIG. 7, but not limited to the embodiment.

Figure 9A:
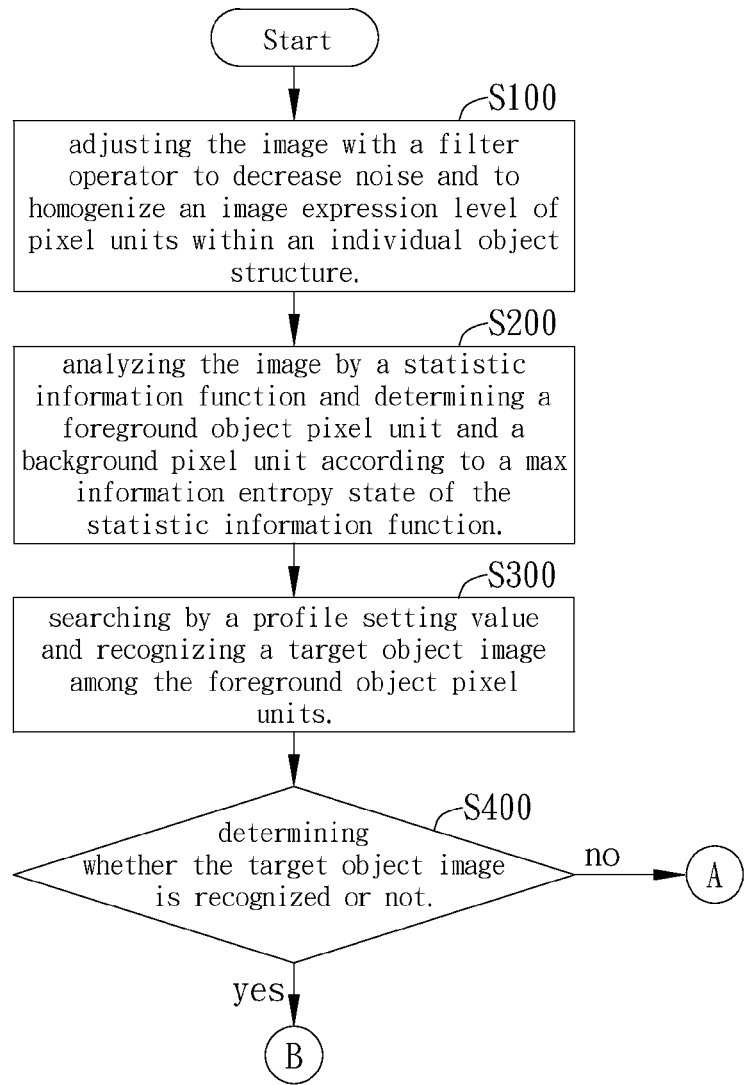
FIG. 9A is a flowchart of another embodiment of the image recognition method of the present invention.
Figure 9B:
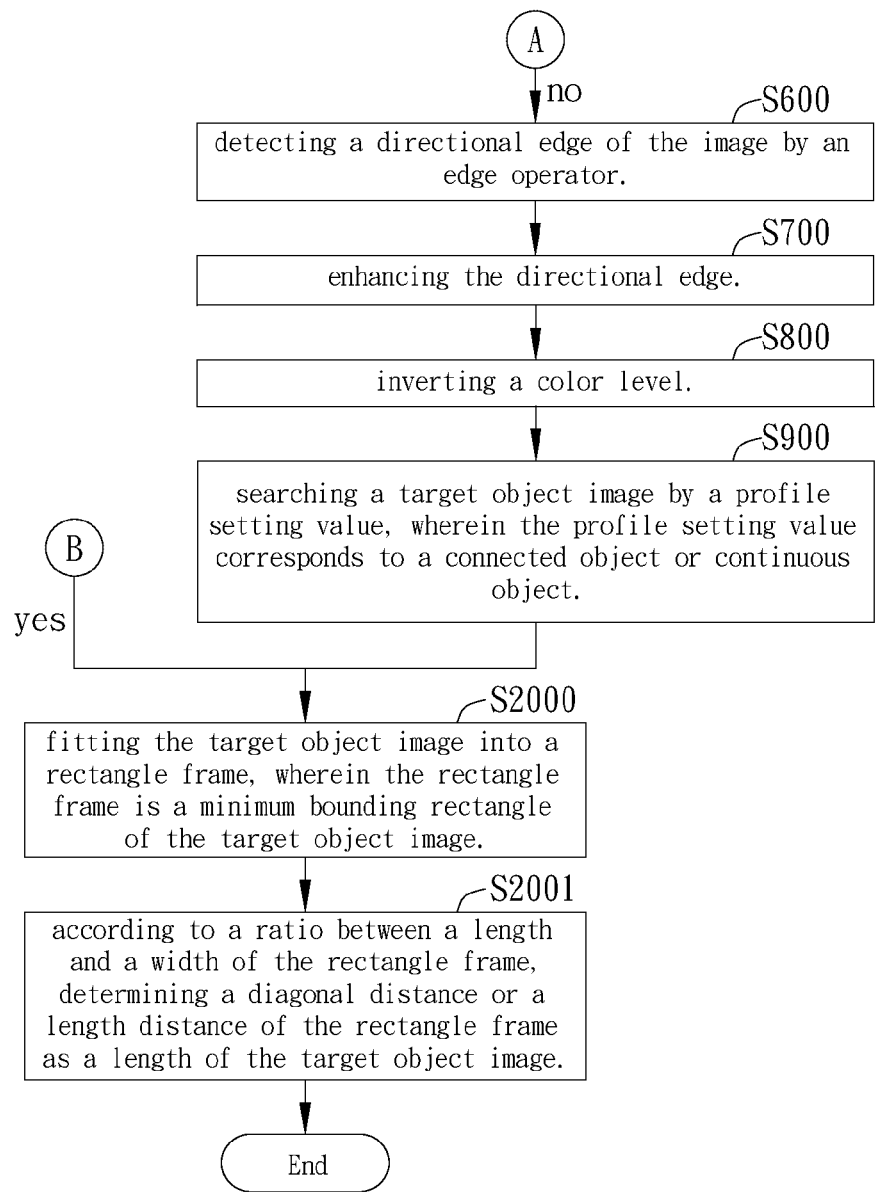
FIG. 9B is a flowchart of another embodiment of the image recognition method of the present invention.
Figure 10A:
FIG. 10A is a schematic view of an embodiment of the image recognition method utilizing the rectangle frame measurement of the present invention.
Figure 10B:
FIG. 10B is a schematic view of another embodiment of the image recognition method utilizing the rectangle frame measurement of the present invention.

It is noted that in addition to the image recognition method of FIGS. 8A and 8B which acquires the length of the target object image by calculations from the coordinate vertexes, the present invention further provides another image recognition method to illustrate other measuring methods. Please refer to FIGS. 9A and 9B; FIG. 9A is a flowchart of another embodiment of the image recognition method of the present invention; FIG. 9B is a flowchart of another embodiment of the image recognition method of the present invention. As shown in FIGS. 9A and 9B, the step S2000 involves fitting the target object image into a rectangle frame, wherein the rectangle frame is a minimum bounding rectangle of the target object image. For instance, as shown in FIGS. 10A and 10B, wherein FIG. 10A is a schematic view of an embodiment of the image recognition method utilizing the rectangle frame measurement of the present invention; FIG. 10B is a schematic view of another embodiment of the image recognition method utilizing the rectangle frame measurement of the present invention. As shown in FIG. 10A, the femur target object image 20A is fitted into the rectangle frame 10A, wherein the rectangle frame 10A is the minimum bounding rectangle of the femur target object image 20A. In another embodiment, as shown in FIG. 10B, the femur target object image 20B is fitted into the rectangle frame 10B, wherein the rectangle frame 10B is the minimum bounding rectangle of the femur target object image 20B.

Then, the image recognition method further executes the step S2001, according to a ratio between a length and a width of the rectangle frame, determining a diagonal distance or a length distance of the rectangle frame as a length of the target object image. For instance, as shown in FIG. 10A, the profile of the rectangle frame 10A has an elongated shape, so the process determines the length distance 200A of the rectangle frame 10A as the length of the femur target object image 20A. In addition, as shown in FIG. 10B, the profile of the rectangle frame 10B is not presented as an appropriate elongated shape, i.e. the ratio of width to length is much higher than FIG. 10A, so the process determines the diagonal distance 200B of the rectangle frame 10B as the length of the femur target object image 20B.

Compared to the step S100 through the step S1001 of FIGS. 8A and 8B, the step S2000 through the step S2001 of FIGS. 9A and 9B utilizes the rectangle frame to measure the length of the target object image, further simplifying the measuring method and increasing measuring efficiency. In practical applications, the image recognition method of FIGS. 9A and 9B can complete the execution of steps S100 through S2001 averagely within 2.28 seconds, but is not limited thereto. In addition, the step S2000 and the step S2001 can be executed in combination with the image recognition methods of FIGS. 1, 3, 6A, 6B, and 7 according to practical requirements to achieve the effect of dimension measurement. Particularly, the step S2000 and the step S2001 can be executed after the step S300 of FIG. 1, the step S300 of FIG. 3, the step S400 or the step S900 of FIGS. 6A and 6B, or the step S900 of FIG. 7, but not limited to the embodiment.

An embodiment of the present invention provides an image recognition system, which is applied to recognize an image, wherein the image includes a plurality of pixel units. In the embodiment, the image can be an ultrasound image, such as fetal ultrasound image, but not limited thereto.

Figure 11:
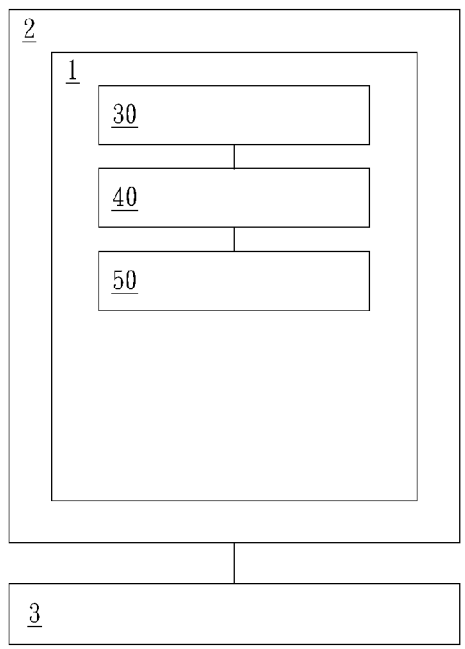
FIG. 11 is a schematic view of an embodiment of an image recognition system of the present invention.

Please refer to FIG. 11; FIG. 11 is a schematic view of an embodiment of an image recognition system of the present invention. In practical applications, the image recognition system 1 can be disposed in a dynamic image reader device 2 or connected with the dynamic image reader device 2, wherein the dynamic image reader device 2 can be an ultrasound image reader device, but not limited to the embodiment. In the embodiment, the image recognition system 1 is disposed in the dynamic image reader device 2, and the dynamic image reader device 2 transmits the image to the image recognition system 1; alternatively, the image recognition system 1 transmits a command to the dynamic image reader device 2, so that the dynamic image reader device 2 transmits the image to the image recognition system 1.

As shown in FIG. 11, the image recognition system 1 includes the image operating module 30, the analysis module 40, and the recognizing module 50. The image operating module 30 has a filter operator, wherein the filter operator adjusts the image to decrease noise and homogenizes an image expression level of the pixel units within an individual object structure.

The analysis module 40 is connected with the image operating module 30 and stores a first operating mode, wherein the first operating mode has a statistic information function. The analysis module 40 analyses the image by the statistic information function and classifies the pixel units into a foreground object pixel unit and a background pixel unit in the first operating mode. The recognizing module 50 is connected with the analysis module 40 and stores a profile setting value, wherein the recognizing module 50 searches and recognizes a target object image among the foreground object pixel units, and the profile setting value corresponds to a connected object.

It is noted that the analysis module 40 normalizes the image to retrieve a plurality of color level values of the pixel units and a display frequency of the color level values and generates a display probability corresponding to the display frequency in the first operating mode. In practical applications, the image includes a plurality of pixel units, wherein the pixel units are pixel elements disposed with matrix arrangement. In an original image, the color variation of the pixel units is extremely large; the image operating module 30 utilizes the filter operator to decrease the variation of the image and to sharpen or smooth the image to simplify the structure information of the image. In practical applications, the filter operator can be an image operating matrix and can adjust color block of each pixel unit, but not limited to the embodiment. In other words, the filter operator can decrease undesired noises of the image and is a pre-process of the image recognition method.

In the embodiment, the image operating module 30 transmits the operated image to the analysis module 40, and the analysis module 40 normalizes the image to retrieve the color level values of the pixel units and the display frequency of the color level values and generates the display probability corresponding to the display frequency. Particularly, the range of the color level values is $0 \sim 2^c - 1$, wherein the color corresponding to the color level value of 0 is black; the color corresponding to the color level value of $2^c - 1$ is white. In the embodiment, the image recognition system 1 utilizes the analysis module 40 to retrieve the color level value of each pixel unit, and the display frequency of each color level value is the frequency of occurrence of each color level value. In addition, for an 8-bit ultrasound image, wherein c=8, and the color level maximum is 255.

In addition, the analysis module 40 generates the display probability corresponding to the display frequency, wherein the probability of occurrence of each color level value is defined as the display probability. In practical applications, the analysis module 40 inputs the color level values and the display probability corresponding to the color level values to the statistic information function. In the embodiment, the statistic information function is the entropy information function, but not limited to the embodiment. Furthermore, the image recognition system 1 utilizes the entropy information function to determine usable pixel units, further recognizing the target object image.

For instance, after the analysis module 40 normalizes the image, the display probability P and the range thereof $p_0 \sim p_{2^c-1}$ can be acquired, wherein the range of the color level value is 0 to $2^c - 1$, and the image entropy H(P) can be given from equations [1]~[4] of the image recognition method. It is noted that, when the statistic information function generates the max information entropy state according to the color level values and the display probability corresponding to the color level values, the analysis module 40 determines the color level value corresponding to the max information entropy state as a color level boundary value. In the embodiment, the analysis module 40 determines the color level value corresponding to the max information entropy state as the color level boundary value when the statistic information function generates the max information entropy state (i.e. the entropy information function generates the max entropy). Furthermore, the analysis module 40 computes the color level boundary value, which can identify classifying the foreground and background, through the equations [1]~[4], further determining the required foreground object pixel unit.

It is noted that the analysis module 40 converts the color level values larger than or equal to the color level boundary value into a color level maximum, and converts the color level values less than the color level boundary value into a color level minimum. It is noted that, when c is 8, the color level maximum is 255, which corresponds to white; the color level minimum is 0, which corresponds to black. For instance, as shown in FIGS. 2A and 2B, the color level values which is larger than or equal to the color level boundary value is converted into white, and the color level values which is less than the color level boundary value is converted into black.

In addition, the recognizing module 50 chooses the pixel units corresponding to the color level maximum to recognize the target object image. It is noted that the target object image includes images of skull, femur, or other organs, wherein each organ corresponds to a profile setting value. For instance, the profile of femur is an elongated structure, and the skull has a circular-like structure, wherein the femur and the skull respectively correspond to a femur profile setting value and a skull profile setting value, so that the image recognition system 1 recognizes the femur target image or the skull target image according to the femur profile setting value and the skull profile setting value. In addition, in the embodiment, the image recognition system 1 can define the profile setting value by two ends of the femur elongated structure having circular profile to recognize the target object image.

For instance of the femur target image, please refer to FIG. 2A through FIG. 2C, wherein FIG. 2A is the schematic view of the original image of the present invention; FIG. 2B is the schematic view of the operated image of the statistic information image of the present invention; FIG. 2C is the schematic view of an image of the recognized target object of the present invention. In practical applications, the user can retrieve the ultrasound image by the dynamic image reader device. FIG. 2A shows the original image of the ultrasound image. It is noted that after the analysis module 40 utilizes the statistic information function to analyze the image, the image shown in FIG. 2B has a clear femur profile and other similar profiles. In addition, after the recognizing module 50 recognizes the image by the profile setting value, the image recognition system 1 can recognize the femur target image as shown in FIG. 2C.

In the embodiment, the analysis module 40 further stores a second operating mode, and the second operating mode has an edge operator. In practical applications, the analysis module 40 detects a directional edge of the image by the edge operator in the second operating mode when the analysis module 40 is unable to recognize the target object image in the first operating mode. The analysis module 40 inverts a color level and searches the target object image by the profile setting value. It is noted that the directional edge can be a horizontal direction edge, a vertical direction edge, or an oblique direction edge. In the embodiment, the directional edge can be a horizontal direction edge. In practical applications, the image operating module 30 may filter out too much effective information, so that the recognizing module 50 is unable to recognize the target object image, and the recognizing module 50 requires to recognize the image in second operating mode again. When the recognizing module 50 is unable to recognize the target object image, the analysis module 40 reads the original image instead of the operated image of the image operating module 30, and the analysis module 40 detects the directional edge of the image by the edge operator in the second operating mode.

It is noted that, in the second operating mode, the analysis module 40 utilizes the original image and can retain details of the original image. In other words, the analysis module 40 computes directly from the color level values of the pixel units of the original image and have high recognition efficiency.

In addition, the edge operator can be a matrix operator, especially is a convolution operator. Detailed descriptions of the correlation between the convolution operator and the image are essentially the same as the edge operator of the image recognition method and not elaborated hereinafter.

It is noted that, after the analysis module 40 detects the edge of the image, the directional edge is stretched to enhance the directional edge. As shown in FIGS. 5A and 5B, after the enhancement, the profile of the directional edge of FIG. 5 is clearly sharper.

Furthermore, the analysis module 40 enhances the directional edge by the equations [5] through [7] of the image recognition method, further increasing the sharpness and the contrast of the structure of directional edge. Detailed descriptions of enhancing the edge are essentially the same as the image recognition method and not elaborated hereinafter.

It is noted that the color level of the femur object of the FIG. 5A is not the same as the color level of the FIG. 5B. As such, the analysis module 40 requires to invert the color level. It is noted that the image includes the pixel units, wherein each pixel unit has the color level value, and the color level value is between a color level maximum and a color level minimum. In practical applications, the analysis module 40 converts the color level value into the color level minimum when the analysis module 40 determines the color level value closer to the color level maximum; the analysis module 40 converts the color level value into the color level maximum if the analysis module 40 determines the color level value closer to the color level minimum.

As described above, the color level maximum is 255, which corresponds to white; the color level minimum is 0, which corresponds to black. In other words, if the original color level value is closer to white, then it is converted into black; if the original color level value is closer to black, then it is converted into white.

In addition, the recognizing module 50 searches the target object image by the profile setting value, wherein the profile setting value corresponds to the connected object or continuous object. Please refer to FIG. 5C; FIG. 5C is the schematic view of an image of the recognized target object of the present invention. In the embodiment, the target object image is the femur, but not limited to the embodiment. As shown in FIGS. 5B and 5C, the femur object of FIG. 5B is a black continuous elongated structure. After the color level is inverted, the femur object of FIG. 5C is a white continuous elongated structure. It is noted that the femur target object image of FIG. 5C is the result after searching by the profile setting value. Detailed descriptions of the profile setting value and the searching process thereof are essentially the same as the image recognition method and not elaborated hereinafter. As shown in FIGS. 5B and 5C, after the analysis module 40 inverts the color level and the recognizing module 50 recognizes the target object, the image recognition system 1 can acquire the precise result. Compared to the first operating mode, the second operating mode can increase the recognition efficiency of the target object image, further increasing the image recognition efficiency.

As shown in FIG. 11, the display device 3 is connected with the dynamic image reader device 2 and the image recognition system 1, wherein the display device 3 displays the dynamic image outputted from the dynamic image reader device 2 and images outputted from the image recognition system 1. In practical applications, the user can receive the original images, the analyzed images, and/or the recognized images from the display device 3, but not limited to the embodiment.

Figure 12:
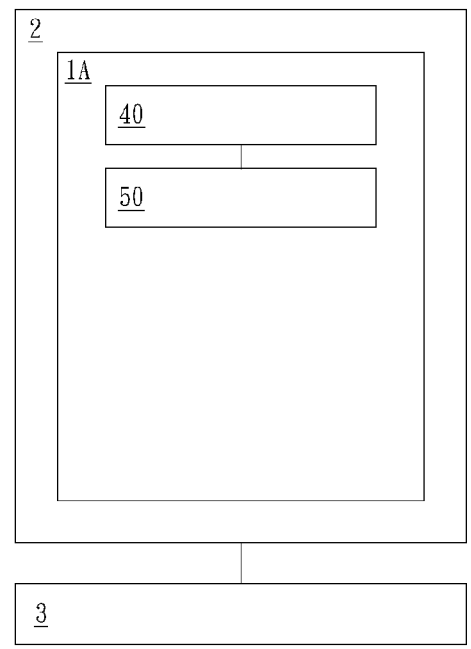
FIG. 12 is a schematic view of another embodiment of the image recognition system of the present invention.

Please refer to FIG. 12; FIG. 12 is a schematic view of another embodiment of the image recognition system of the present invention. Compared to the image recognition system 1, the image recognition system 1A only has the analysis module 40 and the recognizing module 50. In other words, the image recognition system 1A directly utilizes the analysis module 40 to analyze the original image without executing the pre-process of the original image, wherein the analysis can be operated in the second operating mode.

Figure 13:
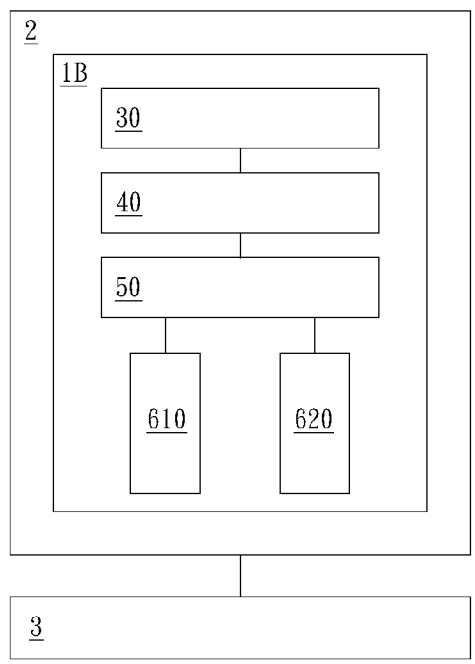
FIG. 13 is a schematic view of another embodiment of the image recognition system of the present invention.

Please refer to FIG. 13; FIG. 13 is a schematic view of another embodiment of the image recognition system of the present invention. Compared to the image recognition system 1, the image recognition system 1B of FIG. 13 further includes the vertex measuring module 610 and the frame measuring module 620. As shown in FIG. 13, the vertex measuring module 610 is connected with the recognizing module 50, wherein the vertex measuring module 610 retrieves a first vertex coordinate and a second vertex coordinate opposite to the first vertex coordinate of the target object image and measures a length of the target object image according to the first vertex coordinate and the second vertex coordinate. Particularly, the recognizing module 50 transmits the target object image to the vertex measuring module 610, and the vertex measuring module 610 measures the length of the target object image according to the first vertex coordinate and the second vertex coordinate. For instance of the femur target object image, the first vertex coordinate and the second vertex coordinate are the coordinates of two ends of the femur object.

Then, the vertex measuring module 610 measures the length of the target object image according to the first vertex coordinate and the second vertex coordinate. For instance, the distance between the first vertex coordinate and the second vertex coordinate can be computed by the distance calculation means, and the image recognition system 1B can acquire the length of the target object image. Particularly, the image recognition system 1B can measure the dimension of the target object image.

In addition, the frame measuring module 620 is connected with the recognizing module 50, wherein the frame measuring module 620 fits the target object image into a rectangle frame, wherein the rectangle frame is a minimum bounding rectangle of the target object image. As shown in FIG. 10A, the femur target object image 20A is fitted into the rectangle frame 10A, wherein the rectangle frame 10A is the minimum bounding rectangle of the femur target object image 20A. In another embodiment, as shown in FIG. 10B, the femur target object image 20B is fitted into the rectangle frame 10B, wherein the rectangle frame 10B is the minimum bounding rectangle of the femur target object image 20B. In practical applications, the frame measuring module 620 determines a diagonal distance or a length distance of the rectangle frame as a length of the target object image according to a ratio between a length and a width of the rectangle frame. For instance, as shown in FIG. 10A, the profile of the rectangle frame 10A has an elongated shape, so the frame measuring module 620 determines the length distance 200A of the rectangle frame 10A as the length of the femur target object image 20A. In addition, as shown in FIG. 10B, the profile of the rectangle frame 10B is not presented as an appropriate elongated shape, i.e. the ratio of width to length is much higher than FIG. 10A, so the frame measuring module 620 determines the diagonal distance 200B of the rectangle frame 10B as the length of the femur target object image 20B.

Figure 14:
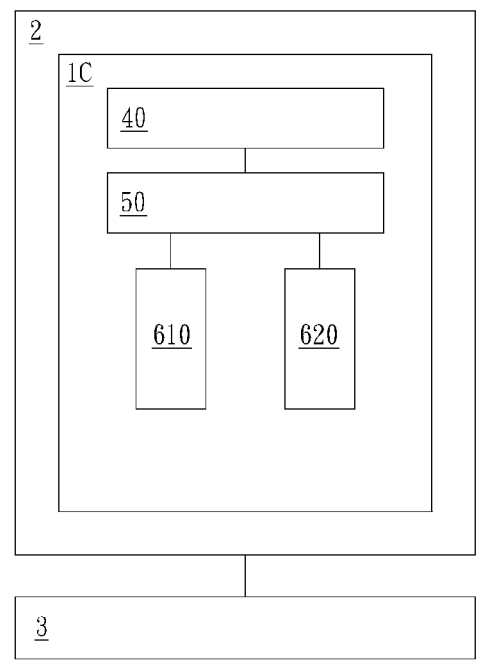
FIG. 14 is a schematic view of another embodiment of the image recognition system of the present invention.

Compared to the vertex measuring module 610, the frame measuring module 620 utilizes the rectangle frame to measure the length of the target object image, further simplifying the measuring method and increasing measuring efficiency. In practical applications, the image recognition system 1B can complete the recognition and measurement of the original image averagely within 2.28 seconds, but is not limited to the embodiment. In addition, please refer to FIG. 14; FIG. 14 is a schematic view of another embodiment of the image recognition system of the present invention. Compared to the image recognition system 1B, the image recognition system 1C only utilizes the second operating mode of the analysis module 40 to analyze the image and utilizes the vertex measuring module 610 or the frame measuring module 620 to measure the target object image, further recognizing and measuring the image. It is noted that, after the image recognition system 1B or the image recognition system 1C measures the length of the target object image, the length information can be transmitted to the display device 3 for user to be easily aware of the result.

It is noted that the image recognition method and the image recognition system of the present invention can be embodied in a computer readable media of computer program product. Furthermore, the present invention provides an image recognition readable media, wherein the image recognition readable media stores the image recognition method or the image recognition system, and the image recognition readable media can recognize images and measure the content of the images.

In other words, the image recognition method and the image recognition system can take the form of an entirely hardware embodiment, an entirely software embodiment (including firmware, resident software, micro-code, etc.), or an embodiment combining software and hardware aspect, e.g. an image recognition electronic module or an image recognition embedded system, but not limited to the embodiment. In practical applications, the image recognition method and the image recognition system of the present invention can take the form of a computer program product embodied in any tangible medium, wherein the computer program product has a plurality of image program codes, and the image program codes include the image recognition method or the image recognition system.

Any combination of one or more computer usable or computer readable media may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java®, Smalltalk, C++ or the like and conventional procedural programming languages, such as the "C" programming language or similar programming languages. ("Java" is a registered trademark of Sun Microsystems, Inc. in the United States, other countries, or both.) The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for instance, through the Internet using an Internet Service Provider).

The present invention is described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Referring now to FIG. 1 through FIG. 14, devices, methods, and computer program products are illustrated as structural or functional block diagrams or process flowcharts according to various embodiments of the present invention. The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which includes one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Compared to prior arts, the image recognition method and the image recognition system of the present invention utilize the statistic information function to define the foreground object pixel unit to recognize the target object image, further increasing image recognition efficiency. In addition, the image recognition method analyzes the image by the edge operator and recognizes the target object image by the profile setting value. In practical applications, the image recognition system has the function of measuring the image, and the completion time of the process of analyzing, recognizing, and measuring is averagely 2.28 seconds.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An image recognition method, executed in an image recognition system, for recognizing objects of interests in an image, wherein the image recognition system has an analysis module, the image recognition method comprising:
    (a) detecting, by the analysis module, a directional edge of the image according to an edge operator;
    (b) enhancing, by the analysis module, the directional edge of the image;
    (c) inverting, by the analysis module, a color level of the image after the directional edge has been enhanced; and
    (d) searching, by the analysis module, for a target object image according to a profile setting value in the image after the color level has been inverted, wherein the profile setting value corresponds to a connected object.

2. The image recognition method of claim 1, wherein the step (b) comprises:
    stretching the directional edge to enhance the directional edge.

3. The image recognition method of claim 1, wherein the image comprises a plurality of pixel units, each pixel unit has a color level value, and the color level value is between a color level maximum and a color level minimum, the step (c) of the image recognition method comprises:
    converting the color level value into the color level minimum if the color level value is closer to the color level maximum; and
    converting the color level value into the color level maximum if the color level value is closer to the color level minimum.

4. The image recognition method of claim 1, after the step (d) further comprising:
    fitting the target object image into a rectangle frame, wherein the rectangle frame is a minimum bounding rectangle of the target object image; and
    determining a diagonal distance or a length distance of the rectangle frame as a length of the target object image according to a ratio between a length and a width of the rectangle frame.

5. An image recognition method, executed in an image recognition system, for recognizing objects of interests in an image comprising a plurality of pixel units, wherein the image recognition system has an analysis module, the image recognition method comprising:
    (a) adjusting, by the analysis module, the image with a filter operator to decrease noise and to homogenize an image expression level of the pixel units within an individual object structure in the image;

(b) analyzing, by the analysis module, according to a statistic information function the image after the image has been adjusted and determining a foreground object pixel unit and a background pixel unit in the image after the image has been adjusted according to a max information entropy state of the statistic information function; and (c) searching, by the analysis module, according to a profile setting value in the image to recognize a target object image among the foreground object pixel unit.

6. The image recognition method of claim 5, wherein the step (b) comprises:

normalizing the image to retrieve a plurality of color level values of the pixel units and a display frequency of the color level values; and generating a display probability corresponding to the display frequency.

7. The image recognition method of claim 6, wherein the step (b) further comprises:

inputting the color level values and the display probability corresponding to the color level values to the statistic information function;

determining the color level value corresponding to the max information entropy state as a color level boundary value when the max information entropy state is generated;

converting the color level values larger than or equal to the color level boundary value into a color level maximum and converting the color level values less than the color level boundary value into a color level minimum to classify the pixel units into the foreground object pixel unit and the background pixel unit; and defining the pixel units corresponding to the color level maximum as the foreground object pixel unit.

8. The image recognition method of claim 5, after step (c) further comprising:

(d1) if the target object image is not recognized, detecting a directional edge of the image by an edge operator;

(d2) enhancing the directional edge;

(d3) inverting a color level; and (d4) searching a target object image by a profile setting value, wherein the profile setting value corresponds to a connected object.

9. The image recognition method of claim 8, wherein the step (d2) comprises:

stretching the directional edge to enhance the directional edge.

10. The image recognition method of claim 8, wherein each pixel unit has a color level value, and the color level value is between a color level maximum and a color level minimum, the step (c) of the image recognition method comprises:

converting the color level value into the color level minimum if the color level value is closer to the color level maximum; and converting the color level value into the color level maximum if the color level value is closer to the color level minimum.

11. The image recognition method of claim 5, after the step (c) further comprising:

retrieving a first vertex coordinate and a second vertex coordinate opposite to the first vertex coordinate of the target object image; and measuring a length of the target object image according to the first vertex coordinate and the second vertex coordinate.

12. The image recognition method of claim 5, after the step (c) further comprising:

fitting the target object image into a rectangle frame, wherein the rectangle frame is a minimum bounding rectangle of the target object image; and according to a ratio between a length and a width of the rectangle frame, determining a diagonal distance or a length distance of the rectangle frame as a length of the target object image.

13. An image recognition system for recognizing objects of interests in an image comprising a plurality of pixel units, the image recognition system comprising:

an image operating module having a filter operator, wherein the filter operator adjusts the image to decrease noise and homogenizes an image expression level of the pixel units within an individual object structure in the image;

an analysis module connected with the image operating module and storing a first operating mode, wherein the first operating mode has a statistic information function, and the analysis module analyses by the statistic information function the image adjusted by the image operating module and classifies the pixel units into a foreground object pixel unit and a background pixel unit in the first operating mode; and a recognizing module connected with the analysis module and storing a profile setting value, wherein the recognizing module searches and recognizes a target object image among the foreground object pixel unit, and the profile setting value corresponds to a connected object.

14. The image recognition system of claim 13, wherein the analysis module normalizes the image to retrieve a plurality of color level values of the pixel units and a display frequency of the color level values and generates a display probability corresponding to the display frequency in the first operating mode.

15. The image recognition system of claim 14, wherein the statistic information function generates the max information entropy state according to the color level values and the display probability corresponding to the color level values, and the analysis module determines the color level value corresponding to the max information entropy state as a color level boundary value, converts the color level values larger than or equal to the color level boundary value into a color level maximum, and converts the color level values less than the color level boundary value into a color level minimum.

16. The image recognition system of claim 13, wherein the analysis module further stores a second operating mode, and the second operating mode has an edge operator; the analysis module detects a directional edge of the image by the edge operator in the second operating mode when the analysis module is unable to recognize the target object image in the first operating mode, and the analysis module inverts a color level and searches the target object image by the profile setting value.

17. The image recognition system of claim 16, wherein the analysis module stretches the directional edge to enhance the directional edge.

18. The image recognition system of claim 16, wherein each pixel unit has a color level value, and the color level value is between a color level maximum and a color level minimum; the analysis module converts the color level value into the color level minimum when the analysis module determines the color level value closer to the color level maximum; the analysis module converts the color level value into the color level maximum if the analysis module determines the color level value closer to the color level minimum.

19. The image recognition system of claim 13, further comprising:

a vertex measuring module connected with the recognizing module, wherein the vertex measuring module retrieves a first vertex coordinate and a second vertex coordinate opposite to the first vertex coordinate of the target object image and measures a length of the target object image according to the first vertex coordinate and the second vertex coordinate.

20. The image recognition system of claim 13, further comprising:

a frame measuring module connected with the recognizing module, wherein the frame measuring module fits the target object image into a rectangle frame, wherein the rectangle frame is a minimum bounding rectangle of the target object image, and the frame measuring module determines a diagonal distance or a length distance of the rectangle frame as a length of the target object image according to a ratio between a length and a width of the rectangle frame.

\* \* \* \* \*